United States Patent [19]

Hayashi

[11] Patent Number: Plant 7,044

[45] Date of Patent: Oct. 3, 1989

[54] ANTHURIUM PLANT NAMED STARLIGHT

[76] Inventor: Calvin K. Hayashi, P.O. Box 242, Pahoa, Hi. 96778

[21] Appl. No.: 237,408

[22] Filed: Aug. 29, 1988

[51] Int. Cl.[4] ..... A01H 5/00

[52] U.S. Cl. ..... Plt./88

[58] Field of Search ..... Plt./88

*Primary Examiner*—Robert E. Bagwill

*Attorney, Agent, or Firm*—Banner, Birch, McKie & Beckett

[57] ABSTRACT

The new Anthurium cultivar named Starlight is characterized by its red-speckled, generally heart-shaped spathe and an indentation along an edge thereof and long, straight pedicles which carry and position the spathe well above the leaves, which are dark green. The new cultivar has a slightly spreading growth habit and an excellent blooming habit.

2 Drawing Sheets

The present invention comprises a new and distinct cultivar of anthurium, botanically known as *Anthurium andraeanum,* and hereinafter referred to by the cultivar name Starlight.

The new cultivar is a product of a planned breeding program, and was originated from a cross made during such a program in Pahoa, Hi., U.S.A. The female, or seed parent was Midori and the male, or pollen plant, was an unnamed red speckled seedling. Starlight was discovered and selected as a flowering plant within the progeny of the stated cross by Calvin K. Hayashi in a controlled environment in Pahoa, Hi., U.S.A. Subsequent asexual reproduction has demonstrated that the combination of characteristics as herein disclosed for the new cultivar are firmly fixed and are retained through successive generation of asexual reproduction.

The following traits have been repeatedly observed and in combination distinguish Starlight as a new and distinct cultivar:

1. The spathe or blossoms are red interspersed with white specks and of large size with a length of 7 inches and a width of 5¾ inches.
2. The shape of the spathe is generally heart-shaped, with one edge slightly indented.
3. The pedicle is straight and strong, and the spathe stand well above the leaves.
4. The leaves are relatively large, dark green in color, with the underside of the leaves being somewhat lighter. New leaves grow at approximately at a 45 degree angle with older leaves set at approximately a 90 degree to 110 degree angle to the pedicle.
5. The new cultivar is slightly spreading in growth habit, being 40 inches in height when grown to maturity in a 10 inch pot.
6. The spadix is approximately 4¼ inches long, 1½ inches in diameter, having a generally yellow color at early growth stages and maturing into an ivory color at maturity.
7. The plant is continuously flowering. When first blooming the spathe are generally small in size and become larger as the plant matures in growth.

The accompanying photographic drawings show a typical specimen of the new cultivar Starlight, with the colors being as nearly true as possible with illustrations of this type. One figure is a front perspective view of the entire plant and the other figure is a close up view of a typical spathe.

The following observations, measurements, and values describe the plant grown in Pahoa, Hi., U.S.A., under greenhouse conditions which closely approximate those generally use in horticultural practice. Color references are made to the *Exotica Horticultural Color Guide,* Series 4, Vol. 2, 1985, except where general color terms of ordinary significance are used.

Botanical classification: *Anthurium andraeanum,* cultivar name, Starlight.

Parentage:

*Male parent.—Anthurium andraeanum* unnamed red-speckled seedling.

*Female parent.—Anthurium andraeanum* Midori.

Propagation: At the present time, propagation is by stem cutting, although tissue culture would be possible with this cutivar.

Plant: When grown in a 10 inch pot the plant is approximately 40 inches tall and approximately 40 inches in diameter.

Leaves:

*Form and size.*—The leaves are generally heart-shaped, with a distinct point. The diameter, depending on the size of the plant, is approximately 14 inches in length and 8½ inches in width.

*Texture.*—Leathery and smooth; slightly shiny in appearance.

*Color.*—Upper side dark green, under side medium green; stems are lighter green than upper side of leaf.

Flowers:

*Buds.*—The spathe is rolled around the spadix; after opening, the spathe stands well above the leaves.

Spathe (blossom):

*Size.*—Approximately 7 inches in length and 5¾ inches in width.

*Color.*—Upperside, 32; Underside 31. The color designation is primarily red with white specks interspersed throughout the spathe.

*Arrangement.*—The spathe stand on long, straight light green pedicels and are at an angle approximately 45 degrees to the pedicle.

*Shape.*—At full bloom, the spathe is generally heart-shaped with the lobes being slightly fused. The veins begin at the base of the spadix and are visible throughout the spathe. The edge of the spathe is indented on one side.

*Texture.*—Glossy.

Reproductive organs:

*Spadix.*—Generally yellow in color maturing to an ivory white.

*Stamens.*—There are four stamens surrounding the pistil. The stamens are visible only when they are separated from the individual reproductive organs from the main axil. The stamens are covered with two small triangular and two square-shaped tops; at the center, the stamen is firmly enclosed.

*Anthers and filaments.*—Not clearly visible.

*Pollen.*—White in color.

*Pistils.*—Grown firmly together with the pulpy main axil and sitting between the stamens. The color is generally yellow, maturing to an ivory white and shaped approximately square, approximately 1/16 of an inch long.

Roots: Very pulpy. New growth is light red in color. Older roots are generally gray.

Disease resistance: Through experiences to date, Starlight exhibits very good tolerance against traditional diseases.

General observations: Starlight is a rapid growing anthurium which under optimum growing conditions produces six to seven blossoms per year. At earlier stages of growth, the plant produces smaller blooms which become larger as the plant matures. The spathe is carried on long, straight pedicels often reaching lengths of 40 inches. The degree of variegation will vary from one flower to the next. This new and distinct cultivar, because of its excellent blooming habit, is well suited for cut flower production as well as a potting plant. Due to this unique combination of characteristics, Starlight provides a valuable new cultivar of *Anthurium andraeanum.*

I claim:

1. A new and distinct cultivar of *Anthurium andraeanum* substantially as described and illustrated, known by the cultivar name Starlight and characterized by the combined features of red speckled, generally heart-shaped spathe and an indentation along an edge thereof; long, straight pedicels which carry and position the spathe well above the leaves; dark green leaves; slightly spreading growth habit and excellent blooming habit.

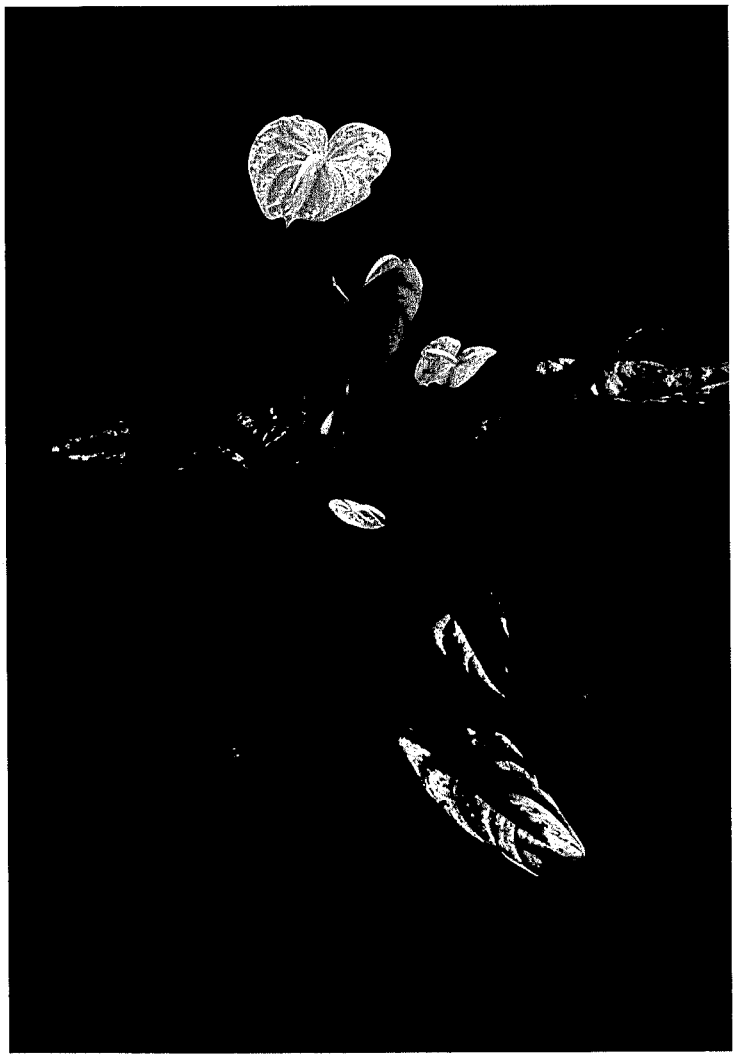

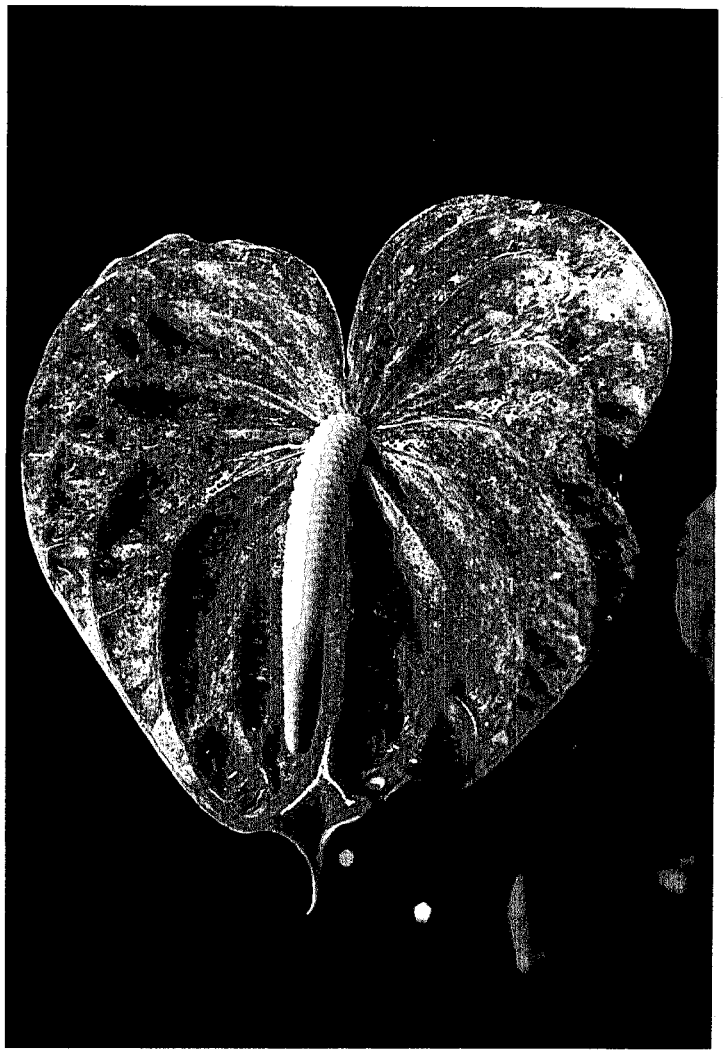

* * * * *